United States Patent
Annergren et al.

(10) Patent No.: US 6,494,989 B2
(45) Date of Patent: Dec. 17, 2002

(54) ABSORBENT PAPER AND A METHOD FOR PRODUCTION THEREOF

(75) Inventors: Jeanette Annergren, Mölnlycke (SE); Holger Hollmark, Stockholm (SE); Ulrika Strandlund, Mölndal (SE)

(73) Assignee: SCA Hygiene Products AB, Gothenburg (SE)

(*) Notice: Subject to any disclaimer, the term of this patent is extended or adjusted under 35 U.S.C. 154(b) by 0 days.

(21) Appl. No.: 09/930,200

(22) Filed: Aug. 16, 2001

(65) Prior Publication Data

US 2002/0060013 A1 May 23, 2002

Related U.S. Application Data

(63) Continuation of application No. PCT/SE00/00528, filed on Mar. 17, 2000.

(30) Foreign Application Priority Data

Mar. 19, 1999 (SE) .............................................. 9900997

(51) Int. Cl.[7] .......................... D21H 17/20; A61L 15/60
(52) U.S. Cl. ............................. 162/168.1; 162/168.3; 162/164.1; 162/164.6; 162/175; 162/179; 162/158; 604/364; 604/367; 428/537.5
(58) Field of Search .................. 162/158, 168.1–168.3, 162/173, 175, 177, 179, 164.1, 164.6, 9, 157.3, 157.6; 604/364–368, 378; 428/537.5, 311.51, 211

(56) References Cited

U.S. PATENT DOCUMENTS

| | | | | |
|---|---|---|---|---|
| 5,149,334 A | * | 9/1992 | Lahrman et al. | ............ 604/367 |
| 5,509,913 A | * | 4/1996 | Yeo | .............................. 604/364 |

FOREIGN PATENT DOCUMENTS

| | | |
|---|---|---|
| EP | 408128 | 1/1991 |
| WO | 9404751 | 3/1994 |
| WO | 9818505 | 5/1998 |

* cited by examiner

Primary Examiner—Jose Fortuna
(74) Attorney, Agent, or Firm—Burns, Doane, Swecker & Mathis, L.L.P.

(57) ABSTRACT

Absorbent wetlaid paper containing at least 1% by weight, calculated on the dry weight of the paper, of an absorbent polymeric material having a thermo-reversible liquid uptake capacity, which has a cloud point, Cp, in water within the temperature interval 30–60° C., preferably 35–55° C., at which the polymer has a substantially higher liquid uptake capacity at temperatures below said cloud point as compared to at temperatures above the cloud point. The thermo-reversible polymer will then be inactive during the paper-making process and be activated to its swelling and absorbent form when it is brought into contact with a liquid, the temperature of which is below the cloud point, Cp, of the polymer.

11 Claims, No Drawings

ABSORBENT PAPER AND A METHOD FOR PRODUCTION THEREOF

This application is a continuation of International Application No. PCT/SE00/00528, filed on Mar. 17. 2000, which International Application was published by the International Bureau in English on Sep. 28. 2000.

TECHNICAL FIELD

The present invention refers to an absorbent wetlaid paper and a method for production thereof. Such a paper is for example used as kitchen rolls, towels, toilet paper, wiping material and in absorbent articles of different kinds, e g diapers, sanitary napkins, panty liners, incontinence guards and bed protections.

BACKGROUND OF THE INVENTION

It is previously known to increase the absorption capacity of paper by mixing different kinds of highly absorbent materials into the pulp. By this it is possible to obtain an absorption capacity of paper that exceeds what can be obtained by using only conventional papermaking fibers. A problem with such an admixture in a wetlaying process is how to avoid swelling of the polymer during the papermaking process. There is for example in EP 0 408 128 disclosed the use in a wetlaying process of a polymer-modified pulp, which in its alkali state swells and absorbs liquid. The wetlaying process is performed without the presence of disturbing alkali metal ions and the polymer is used in its protonized form, at which the partly dewatered paper web is brought into contact with alkali metal ions in order to activate the polymer. This involves a complicated and sensitive process.

OBJECT AND MOST CHARACTERISTIC FEATURES OF THE INVENTION

The object of the present invention is to provide a wetlaid paper with improved absorption properties, which can be produced in a simple way with a conventional wetlaying process without complicated additional process steps. This has according to the invention been solved by the fact that the paper contains at least 1% by weight, calculated on the dry weight of the paper, of an absorbent polymeric material having a thermo-reversible liquid uptake capacity, which has a cloud point, Cp, in water within the temperature interval 30–60° C., preferably 35–55° C., at which the polymer has a substantially higher liquid uptake capacity at temperatures below said cloud point as compared to at temperatures above the cloud point.

As the papermaking process at the wet end normally is run at temperatures above about 45–60° C. the thermo-reversible polymer will be inactive during the papermaking process and be activated to its swelling and absorbent form when it is brought to contact with a liquid the temperature of which is below the cloud point, Cp, of the polymer.

A polymer having a thermo-reversible liquid uptake capacity is characterized by that the polymer at a certain temperature changes its geometrical configuration, at which the hydrophilic and hydrophobic groups of the polymers take another position, resulting in that the liquid uptake capacity of the polymer is considerably changed. Thermo-reversible polymers thus at a specific temperature has a cloud point, Cp, at which the liquid uptake capacity of the polymer is changed. The cloud point, Cp, is in the interval 30–60° C., preferably 35–55° C., for the polymers that have been found suitable for use in the present invention.

The paper preferably contains at least 3% by weight and preferably at least 4% by weight of said thermo-reversible polymeric material.

The absorbent thermo-reversible polymeric material is preferably in the form of fibers in order to simplify its admixture into the pulp structure. It is however also possible that the material is present in another particulate form, e.g. as flakes, powder or the like.

The absorbent thermo-reversible polymeric material can be any of the following materials: crosslinked ethyl hydroxy ethyl cellulose (EHEC), crosslinked polyvinyl methyl ether (PVME), crosslinked polymers of acrylamide, starch derivatives, polymeric tensides, polyethylene glycols and copolymers thereof.

The crosslinked polymer of acryl amide can be poly-n-isopropyl acryl amide, poly-n-n-polymethacryl amide and/or poly-n-n-diethyl acryl amide.

The absorbent thermo-reversible polymeric material is preferably at least partly based on a renewable raw material.

The invention further refers to a method of producing an absorbent wetlaid paper, by adding an absorbent thermo-reversible polymeric material of the above mentioned kind to the pulp suspension, producing a wetlaid paper web of the pulp suspension to which the thermo-reversible material has been added, and then dewatering and drying the wetlaid paper web.

The thermo-reversible polymeric material is added to the pulp suspension preferably in the form of dry fibers.

The temperature of the pulp suspension is during the wet end of the papermaking process kept above the cloud point of the thermo-reversible material.

DESCRIPTION OF THE INVENTION

According to the invention the paper should contain at least 3% by weight and preferably at least 4% by weight calculated on the dry weight of the paper, of an absorbent polymeric material having a thermo-reversible water uptake capacity. The thermo-reversible material should have a cloud point, Cp, in water within the temperature interval 30–60° C., preferably 35–55° C., and should have a substantially higher water uptake capacity at temperatures below said cloud point than above the cloud point. Cloud point here refers to the cloud point in distilled water, since the cloud point changes when electrolytes and other substances are added to the water.

The thermo-reversible material can consist of a cellulose derivative such as a crosslinked ethyl hydroxy ethyl cellulose (EHEC), a crosslinked polyvinyl methyl ether (PVME), crosslinked polymers of acryl amide, starch derivatives, polymeric tensides, polyethylene glycols and copolymers thereof, having the desired thermo-reversibility.

The absorbent thermo-reversible polymeric material can consist of a crosslinked copolymer containing acryl amide and a carboxy containing vinyl monomer such as acrylic acid. It could also consist of a crosslinked copolymer containing acryl amide and a sulphonic acid containing monomer.

As crosslinkers most types of common crosslinkers could be used. The degree of crosslinking effects the absorption properties and gel strength of the material.

Examples of useful polymers are:

A: EHEC (ethyl hydroxy ethyl cellulose) with the cloud point (Cp) 36.1° C. was crosslinked with 4 mole-% divinyl sulphone. The cloud point in distilled water was measured to 40° C. and in synthetic urine to 38° C.

B: EHEC (ethyl hydroxy ethyl cellulose) with the cloud point (Cp) 38.7° C. was crosslinked with 4 mole-% DVS (divinyl sulphone). The cloud point in distilled water was measured to 43° C. and in synthetic urine to 40° C.

C: p(NIPA-co-AANa) 98/2, a copolymer of 98% by weight n-isopropyl acryl amide and 2% by weight sodium acrylate, was crosslinked with 0.3 mole-% MBA (methylene bisacrylamide). The cloud point in distilled water was measured to 47° C. and in synthetic urine to 34° C.

D: p(NIPA-co-AMPSNa) 98/2, a copolymer of 98% by weight n-isopropyl acryl amide and 2% by weight sodium acryl amide methane propane sulphonic acid, was crosslinked with 0.3 mole-% MBA (methylene bisacryl amide). The cloud point in distilled water was measured to 48° C. and in synthetic urine to 35° C.

The rest of the material comprised in the paper is conventional pulp fibers of optional kind such as for example chemical pulp, mechanical pulp, thermo mechanical pulp, chemothermomechanical pulp (CTMP) and recycled pulp. The paper could also contain different kinds of additions such as filling agents, bonding agents, wet strength agents, dry strength agents, softening agents and the like.

The thermo-reversible polymeric material is preferably present in the form of fibers, but could also be present in another particulate form, such as flakes or powder. It is mixed into then pulp suspension before formation of the paper web. The temperature of the pulp suspension in a papermaking process is usually between 45 and 60° C., at which the thermo-reversible polymeric material will be present in its inactive non-absorbent form and thus not disturb the papermaking process. The paper web is formed, dewatered and dried in a usual way.

It is of course also possible in connection with a multilayer process to add the thermo-reversible polymeric material only to one or more layer(s).

When the paper according to the invention is used to absorb liquids at a temperature below the cloud point of the thermo-reversible polymeric material this will be activated and swell while absorbing liquid. The absorption capacity of the paper can by this be significantly increased as compared to a paper only containing pulp fibers.

The paper according to the invention can be used in kitchen rolls, towels, wiping material and as absorption material in absorbent article such as diapers, sanitary napkins, panty liners, incontinence guards, bed protections and the like.

What is claimed is:

1. An absorbent wetlaid paper comprising at least 1% by weight, calculated on the dry weight of the paper, of an absorbent polymeric material having a thermo-reversible liquid uptake capacity, which has a cloud point, Cp, in water within the temperature interval 30–60° C., at which the polymer has a substantially higher liquid uptake capacity at temperatures below said cloud point as compared to at temperatures above the cloud point.

2. The paper as claimed in claim 1, wherein the paper contains at least 3% by weight of said absorbent thermo-reversible polymeric material.

3. The paper as claimed in claim 1, wherein the absorbent thermo-reversible polymeric material is in the form of fibers.

4. The paper as claimed in claim 1, wherein the absorbent thermo-reversible polymeric material is any of the following materials: crosslinked ethyl hydroxy ethyl cellulose (EHEC), crosslinked polyvinyl methyl ether (PVME), crosslinked polymers of acrylamine, starch derivatives, polymeric tensides, polyethylene glycols and copolymers containing any of these.

5. The paper as claimed in claim 4, wherein the crosslinked polymer of acrylamine is poly-n-isopropyl acryl amide, poly-n-n-polymethacryl amide or poly-n-n-diethylacryl amide.

6. The paper as claimed in claim 1, wherein the absorbent thermo-reversible polymeric material comprises at least partly renewable raw materials.

7. The paper as claimed in claim 1, wherein the cloud point is within the temperature interval 35–55° C.

8. The paper as claimed in claim 1, wherein the paper contains at least 4% by weight of said absorbent thermo-reversible polymeric material.

9. A method for producing an absorbent wetlaid paper, comprising adding to a pulp suspension an absorbent polymeric material having a thermo-reversible liquid uptake capacity, which has a cloud point, Cp, in water within the temperature interval 30–60° C., at which the polymer has a substantially higher liquid uptake capacity at temperatures below said cloud point as compared to at temperatures above the cloud point, keeping the temperature of the pulp suspension during the wet end of the papermaking process at a level above the cloud point of the thermo-reversiblle material, producing a wetlaid paper web from said pulp suspension to which the thermo-reversible polymeric material has been added and dewatering and drying the wetlaid paper web.

10. The method as claimed in claim 9, wherein the adding step includes adding the thermo-reversible polymeric material to the pulp suspension in the form of dry fibers.

11. The method as claimed in claim 9, wherein the cloud point is within the temperature interval 35–55° C.

* * * * *